(12) United States Patent
Chen et al.

(45) Date of Patent: Feb. 2, 2021

(10) Patent No.: US 10,905,353 B2

(54) MAGNETIC RESONANCE IMAGING

(71) Applicant: SHANGHAI NEUSOFT MEDICAL TECHNOLOGY CO., LTD., Shanghai (CN)

(72) Inventors: Cao Chen, Shanghai (CN); Hongyu Guo, Shanghai (CN); Qin Xu, Shanghai (CN)

(73) Assignee: Shanghai Neusoft Medical Technology Co., Ltd., Shanghai (CN)

(*) Notice: Subject to any disclaimer, the term of this patent is extended or adjusted under 35 U.S.C. 154(b) by 525 days.

(21) Appl. No.: 15/725,065

(22) Filed: Oct. 4, 2017

(65) Prior Publication Data
US 2018/0098712 A1    Apr. 12, 2018

(30) Foreign Application Priority Data
Oct. 8, 2016  (CN) .......................... 2016 1 0879030

(51) Int. Cl.
*A61B 5/055*     (2006.01)
*G01R 33/565*    (2006.01)
(Continued)

(52) U.S. Cl.
CPC .......... *A61B 5/055* (2013.01); *G01R 33/5608* (2013.01); *G01R 33/5615* (2013.01); *G01R 33/5617* (2013.01); *G01R 33/56554* (2013.01)

(58) Field of Classification Search
CPC ............... A61B 5/055; G01R 33/5608; G01R 33/5615; G01R 33/5617; G01R 33/56554
See application file for complete search history.

(56) References Cited

U.S. PATENT DOCUMENTS

| 5,615,676 A | 4/1997 | Kohno |
| 6,664,787 B2 | 12/2003 | Miyoshi et al. |

(Continued)

FOREIGN PATENT DOCUMENTS

| CN | 1120673 A | 4/1996 |
| CN | 1350176 A | 5/2002 |

(Continued)

OTHER PUBLICATIONS

State Intellectual Property Office of the People's Republic of China, Office Action and Search Report Issued in Application No. 201610879030.3, dated Jul. 30, 2018, 13 pages. (Submitted with Partial Translation).

*Primary Examiner* — Patrick Assouad
*Assistant Examiner* — Haidong Zhang
(74) *Attorney, Agent, or Firm* — McCoy Russell LLP

(57) ABSTRACT

A magnetic resonance imaging (MRI) method is provided. The method includes: a first echo signal and a second echo signal generated from each of channels of a MRI device are acquired by performing a pre-scanning according to an imaging sequence; a correction displacement with which an imaging phase consistency is maximum is determined by shifting a signal curve of the second echo signal for each of the channels for a plurality of times; a one-order phase correction value and a zero-order phase correction value for the channels are determined under the imaging sequence according to the correction displacement; a formal scanning is performed according to the imaging sequence to obtain scanning data; and a phase correction is performed on the scanning data according to the one-order phase correction value and the zero-order phase correction value to obtain target scanning data for reconstructing an image.

16 Claims, 7 Drawing Sheets

(51) Int. Cl.
    *G01R 33/561*    (2006.01)
    *G01R 33/56*    (2006.01)

(56) References Cited

U.S. PATENT DOCUMENTS

| | | |
|---|---|---|
| 6,703,834 B2 | 3/2004 | Ikezaki |
| 2002/0050816 A1 | 5/2002 | Miyoshi |
| 2009/0134871 A1* | 5/2009 | Yui .................... G01R 33/5614 324/309 |
| 2009/0195247 A1* | 8/2009 | Pfeuffer ............. G01R 33/5616 324/307 |
| 2011/0291651 A1* | 12/2011 | Umeda ............ G01R 33/56554 324/307 |
| 2011/0291653 A1* | 12/2011 | Umeda .............. G01R 33/5617 324/309 |
| 2016/0363643 A1* | 12/2016 | Umeda .............. G01R 33/5617 |

FOREIGN PATENT DOCUMENTS

| | | |
|---|---|---|
| CN | 1350831 A | 5/2002 |
| CN | 1378816 A | 11/2002 |
| CN | 101498774 A | 8/2009 |
| CN | 104569882 A | 4/2015 |
| CN | 105247382 A | 1/2016 |
| JP | 2001292976 A | 10/2001 |

* cited by examiner

MAGNETIC RESONANCE IMAGING

CROSS REFERENCE TO RELATED APPLICATIONS

This application claims priority to Chinese Patent Application No. 201610879030.3 filed on Oct. 8, 2016. The entire content of the above-cited application is incorporated herein by reference for all purposes.

BACKGROUND

The present disclosure relates to magnetic resonance imaging.

Magnetic resonance imaging is a technology by which imaging is performed according to resonance characteristics of a bio-magnetic nucleon in a magnetic field. Since the magnetic resonance imaging may cause no lasting effects to a subject without ionizing radiation, it is widely used in clinical medicine.

NEUSOFT MEDICAL SYSTEMS CO., LTD. (NMS), founded in 1998 with its world headquarters in China, is a leading supplier of medical device, medical IT solutions, and healthcare services. NMS supplies medical device with a wide portfolio, including CT, magnetic resonance imaging, digital X-ray machine, ultrasound, Positron Emission Tomography (PET), Linear Accelerator (LINAC), and biochemistry analyser. Currently, NMS' products are exported to over 60 countries and regions around the globe, serving more than 5,000 renowned customers. NMS's latest successful developments, such as 128 Multi-Slice CT Scanner System, Superconducting magnetic resonance imaging, LINAC, and PET products, have led China to become a global high-end medical device producer. As an integrated supplier with extensive experience in large medical device, NMS has been committed to the study of avoiding secondary potential harm caused by excessive X-ray irradiation to the subject during the CT scanning process.

DETAILED DESCRIPTION

Figure 1:
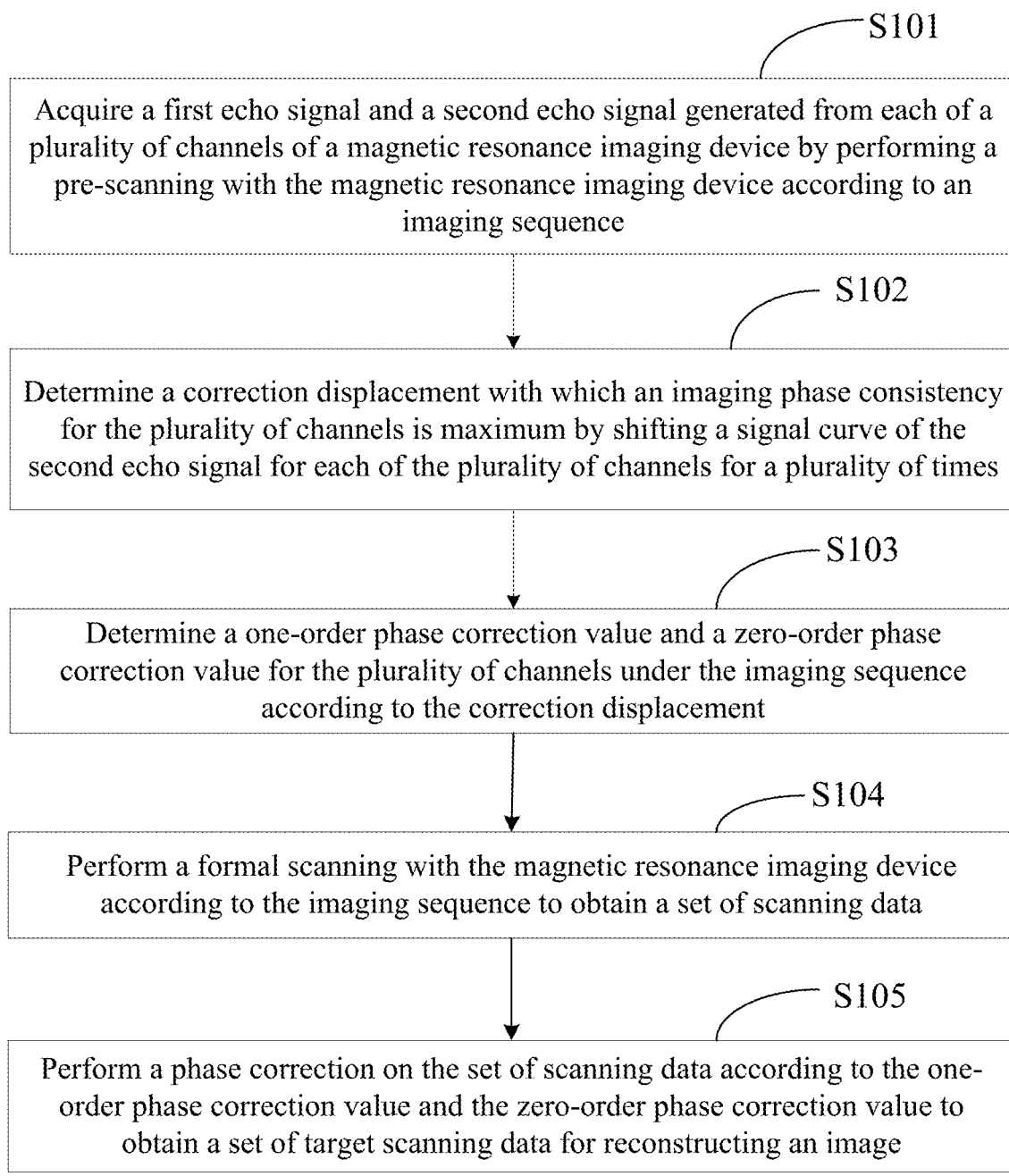
FIG. 1 illustrates a schematic flow chart of a magnetic resonance imaging method according to one or more examples of the present disclosure.

In magnetic resonance imaging, an image may be reconstructed by collecting magnetic resonance signals. For most imaging sequences, a Fast Fourier Transformation (FFT) algorithm may be used to reconstruct an image. The algorithm may function under the condition that the magnetic resonance signals collected repeatedly have the same initial phase to increase a signal-to-noise ratio or reduce artifacts. It is noted that an imaging sequence refers to a combination of radio frequency pulses and gradient pulses both having a particular bandwidth and a particular amplitude, and the radio frequency pulses and the gradient pulses may be formed into different imaging sequences by different combining manners.

For a Turbo Spin Echo (TSE) sequence, when signals collected by a magnetic resonance imaging device is a superimposition of a Spin Echo (SE) signal and a Stimulated-Echo (STE) signal, since generation mechanisms of the two signals are different, phases of the two signal may be unsynchronized. In this way, the intensity of the two signals may be offset each other, which may cause the reconstructed image to darken, etc. For an Echo Planar Imaging (EPI) sequence, when the magnetic resonance imaging device collects signals, it may use alternating positive and negative to read-out gradient magnetic fields. The positive gradient magnetic field and the negative gradient magnetic field may have different durations and amplitudes, etc., which may cause unsynchronized phases of the collected signals and N/2 artifacts.

According to these cases, a pre-scanning may be performed before a formal scanning to obtain pre-scanning data. A phase may be obtained by the pre-scanning data and then the obtained phase may be corrected. In this way, the influence from the unsynchronized phases may be eliminated. A higher-order phase difference, a one-order phase difference and a zero-order phase difference may contribute to the unsynchronized phases. In an example, since the higher-order phase difference is relatively smaller, a method of compensating the higher-order phase difference is relatively complex, and comparing with the higher-order phase difference, the one-order phase difference and the zero-order phase difference may be greater. When correcting the unsynchronized phases, only the one-order phase difference and the zero-order phase difference of the two signals may be considered. Where, the one-order phase difference may be indicated by delays of the two signals in time, and the zero-phase difference may be indicated by an initial phase difference between the two signals. It is noted that the magnetic resonance imaging device may obtain the one-order phase difference according to delays of the two signals in time. In an example, the unsynchronized phases may be corrected according to the zero-order phase difference and the one-order phase difference. Hereinafter, the one-order phase difference may also be referred to as a one-order phase correction value, and the zero-order phase difference may also be referred to as a zero-order phase correction value.

In an example, a method of correcting the unsynchronized phases may include: determining a region in the vicinity of the maximum value of a signal, and taking a moment corresponding to the center of gravity of the region as a fully focusing moment of the signal. A difference between the moments corresponding to the centers of gravity of two signals may be a time difference corresponding to the one-order phase difference in time. The one-order phase difference may be obtained according to the time difference corresponding to the one-order phase difference in time. A zero-order phase difference may be a phase difference corresponding to the fully focusing moment of the two signals. However, in this method of correcting the unsynchronized phases, when the one-order phase difference is wrong, a zero-order phase correction value may also be wrong. Since the one-order phase difference is associated with signals of an entire scanning region of a subject and susceptible to magnetic field uniformity, etc., when imaging with a receiving coil having a plurality of channels, the obtained one-order phase correction value may be wrong. In an example, a channel may refer to a data channel. For example, when the abdomen of the subject receives a magnetic resonance scanning, the magnetic resonance imaging device may receive data sent from different sensors. A sensor may correspond to one or more data channels.

FIG. 1 illustrates a schematic flow chart of a magnetic resonance imaging method according to one or more examples of the present disclosure. The magnetic resonance imaging method of the present disclosure may include the following steps S101-S105.

At step S101, a first echo signal and a second echo signal generated from each of a plurality of channels of a magnetic resonance imaging device are acquired by performing a pre-scanning with the magnetic resonance imaging device according to an imaging sequence.

Here, the first echo signal and the second echo signal may be generated by different pulse combinations in the imaging sequence.

At step S102, a correction displacement with which an imaging phase consistency for the plurality of channels, which may be a maximum, may be determined by shifting a signal curve of the second echo signal for each of the plurality of channels for a plurality of times, where the imaging phase consistency indicates a phase consistency degree between the first echo signal and the shifted second echo signal for each of the plurality of channels.

At step S103, a one-order phase correction value and a zero-order phase correction value for the plurality of channels under the imaging sequence may be determined according to the correction displacement.

At step S104, a formal scanning may be performed with the magnetic resonance imaging device according to the imaging sequence to obtain a set of scanning data.

At step S105, a phase correction may be performed on the set of scanning data according to the one-order phase correction value and the zero-order phase correction value to obtain a set of target scanning data for reconstructing an image.

The one-order phase correction value and the zero-order phase correction value for the plurality of channels may be determined by shifting a signal curve in the magnetic resonance imaging method of the present disclosure, instead of determining the one-order phase correction value based on a signal shape. In this way, the correctness and robustness of the one-order phase correction value and the zero-order phase correction value under the plurality of channels can be improved, thereby improving the image quality of magnetic resonance imaging.

At the above step S102, shifting the signal curve of the second echo signal for each of the channels for a plurality of times includes: providing a plurality of alternative displacements; and shifting the signal curve of the second echo signal for each of the plurality of channels according to each of the plurality of the alternative displacements. During one shift, the displacement for the signal curve of the second echo signal for each of the plurality of channels is the same. It is noted that for each shift, the displacement for the signal curve of the second echo signal for one channel is different, but during one shift, the displacement for the signal curve of the second echo signal for each of the plurality of channels is the same.

Figure 2:
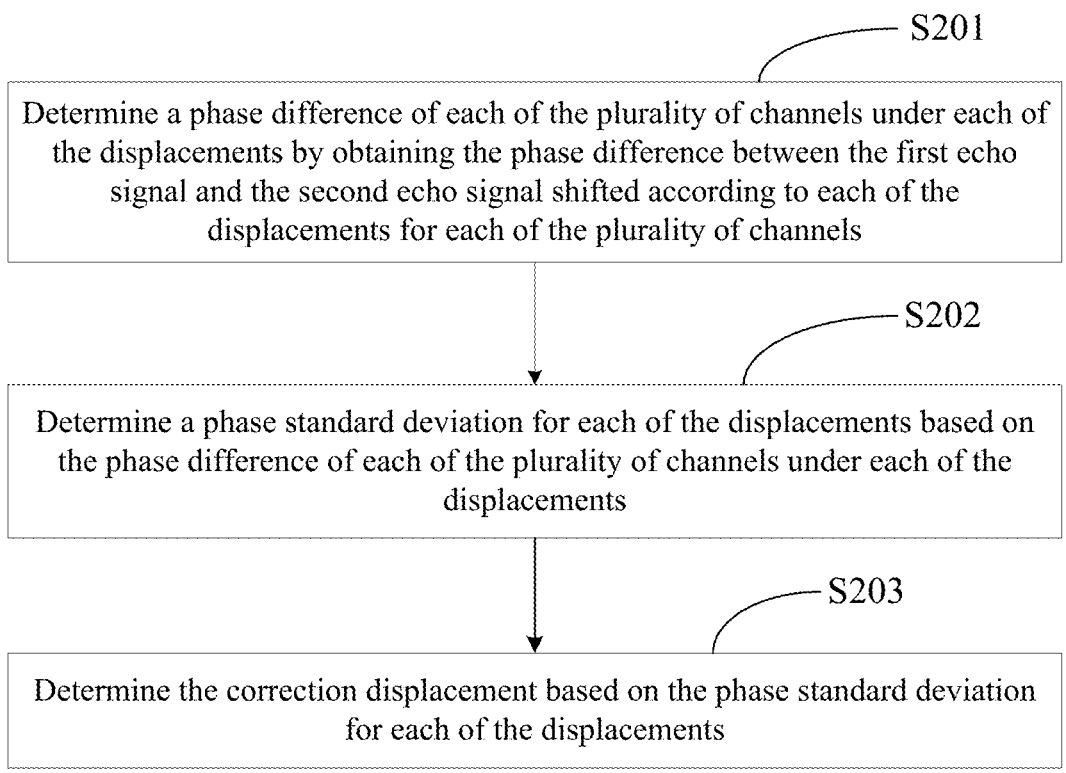
FIG. 2 illustrates a schematic flow chart of a method of determining a correction displacement according to one or more examples of the present disclosure.

FIG. 2 illustrates a schematic flow chart of a method of determining a correction displacement according to one or more examples of the present disclosure. Determining a correction displacement includes the following steps S201-S203.

At step S201, a phase difference of each of the plurality of channels under each of the displacements may be determined by obtaining the phase difference between the first echo signal and the second echo signal shifted according to each of the displacements for each of the plurality of channels.

At step S202, a phase standard deviation for each of the displacements may be determined based on the phase difference of each of the plurality of channels under each of the displacements.

At step S203, the correction displacement may be determined based on the phase standard deviation for each of the displacements.

According to an example, the magnetic resonance imaging method may further include: setting a signal-to-noise ratio threshold, and selecting channels having a signal-to-noise ratio higher than the signal-to-noise ratio threshold from all the channels of the magnetic resonance imaging device as the plurality of channels. In this way, the first echo signal and the second echo signal for a part of invalid channels may be filtered out to reduce the calculation amount and improve the efficiency.

Figure 3:
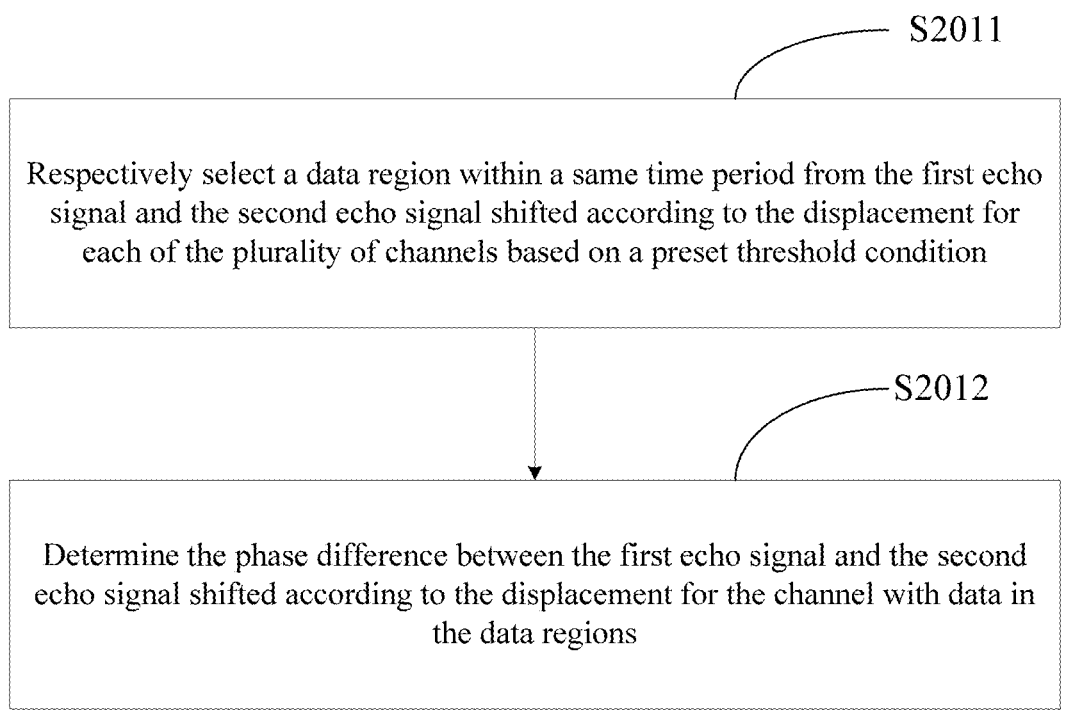
FIG. 3 illustrates a detailed flow chart of step S201 in FIG. 2.

FIG. 3 illustrates a detailed flow chart of step S201 of FIG. 2. In one or more examples of the present disclosure, the step S201 described above further includes the following blocks S2011-S2012.

At step S2011, a data region within a same time period may be respectively selected from the first echo signal and the second echo signal shifted according to the displacement for each of the plurality of channels based on a preset threshold condition.

At block S2012, the phase difference between the first echo signal and the second echo signal shifted according to the displacement for the channel may be determined with data in the data regions.

In one or more examples of the present disclosure, the data in the data regions includes two or more sets of data selected from a data window within any one or more of the data regions. In one or more examples, the preset threshold condition may be 10% to 20% of a maximum amplitude of the first echo signal or the second echo signal.

In one or more examples of the present disclosure, the phase difference between the first echo signal and the second echo signal shifted according to the displacement for each of the plurality of channels may be determined with a weighted summation method. However, it is noted that the present disclosure is not limited to the weighted summation method, and other summation methods may be used, as long as the phase difference between the first echo signal and the second echo signal shifted according to the displacement for each of the plurality of channels under each of the displacements can be determined.

At the step S102 described above, determining the correction displacement based on the phase standard deviation for each of the displacements may include: determining a displacement corresponding to a minimum value among the phase standard deviations (hereinafter may be referred to as a minimum standard deviation) as a first displacement; determining two displacements respectively before and after the first displacement, as a second displacement and a third displacement, respectively; obtaining a fitting curve by performing a curve fitting with the first displacement, the second displacement, the third displacement and respective phase standard deviations corresponding to the first displacement, the second displacement, the third displacement; and taking a displacement corresponding to a minimum standard deviation on the fitting curve as the correction displacement.

In one or more examples of the present disclosure, the curve fitting may be performed with a quadratic curve fitting method. However, it is noted that the present disclosure is not limited to the quadratic curve fitting method. Other curve fitting methods may also be used, as long as the curve fitting can be performed with the first displacement, the second displacement, the third displacement and respective phase standard deviations corresponding to the first displacement, the second displacement, the third displacement.

Figure 4:
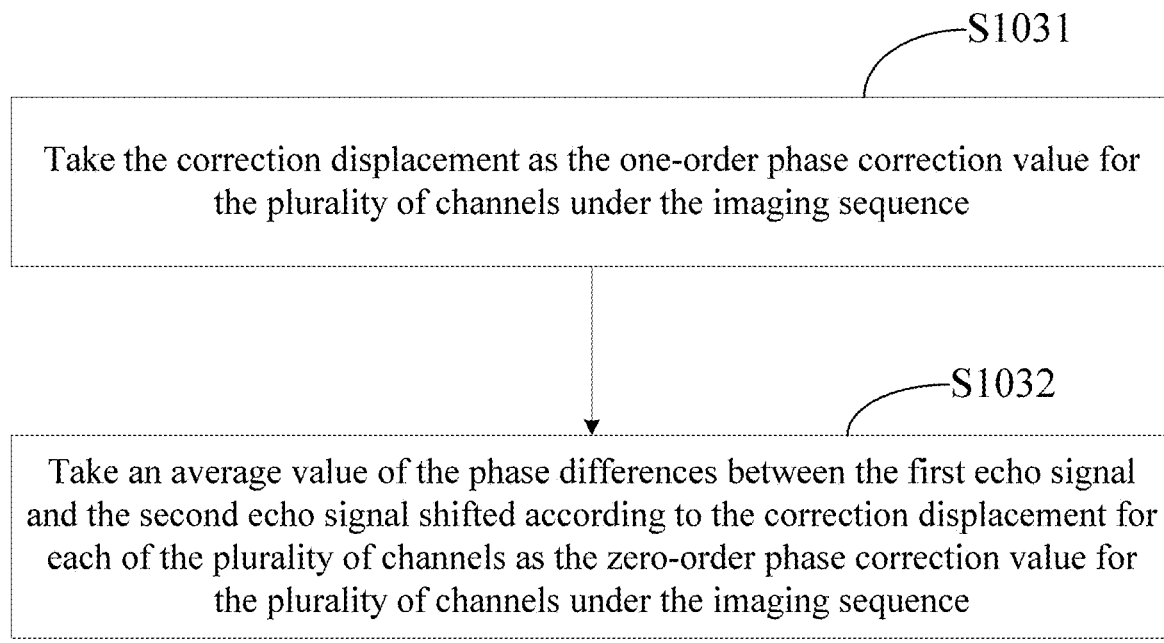
FIG. 4 illustrates a detailed flow chart of step S103 in FIG. 1.

FIG. 4 illustrates a detailed flow chart of step S103 of FIG. 1. In one or more examples of the present disclosure, the step S103 described above may further include the following steps S1031-S1032.

At step S1031, the correction displacement may be taken as the one-order phase correction value for the plurality of channels under the imaging sequence.

At step S1032, an average value of the phase differences between the first echo signal and the second echo signal shifted according to the correction displacement for each of the plurality of channels may be taken as the zero-order phase correction value for the plurality of channels under the imaging sequence.

In a data processing method based on k space (may also be referred to as Fourier Space), when the one-order phase difference is correct, the phase difference of two signals is a constant and the phase differences of different channels may be highly consistent at this time. According to the above characteristics, in the magnetic resonance imaging method of the present disclosure, instead of determining the one-order phase correction value based on the signal shape, the one-order phase correction value and the zero-order phase correction value for the plurality of channels may be determined by shifting the signal curve, which is similar to determine the zero-order phase correction value under different one-order phase correction values. Since the zero-order phases for each of the channels should remain consistent, a value close to the one-order phase correction value may be obtained by shifting the signal curve. Finally, the one-order phase correction value may be obtained with the fitting method. Therefore, the magnetic resonance imaging method of the present disclosure can improve the correctness and robustness of the one-order phase correction value and the zero-order phase correction value under the plurality of channels, thereby improving the image quality of magnetic resonance imaging.

Hereinafter, the magnetic resonance imaging method in the present disclosure will be described by one or more examples. In the following examples, the magnetic resonance imaging sequence is a turbo spin echo sequence, the number of channels is 7 (channels 1 to 7), the times of shifts is 5, and the displacements of the 5 shifts are 1 to 5, respectively. Correspondingly, the first echo signal is a spin echo signal and the second echo signal is a stimulated-echo signal.

Figure 5:
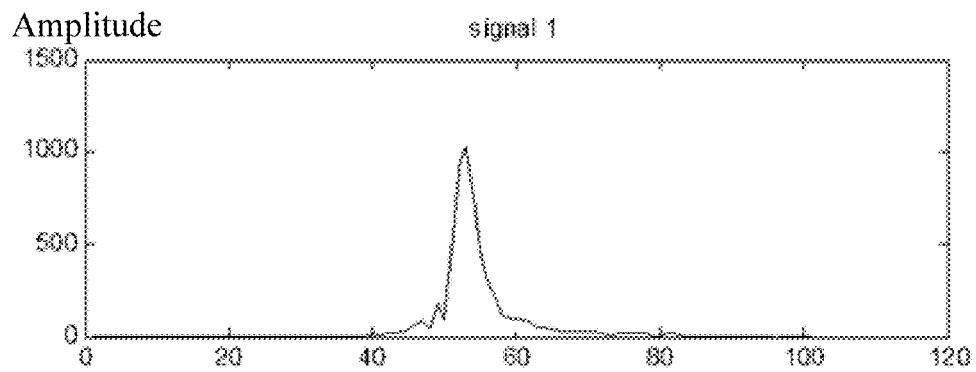
FIG. 5 illustrates waveform diagrams of echo signals in a magnetic resonance imaging method according to one or more examples of the present disclosure.
Figure 5:
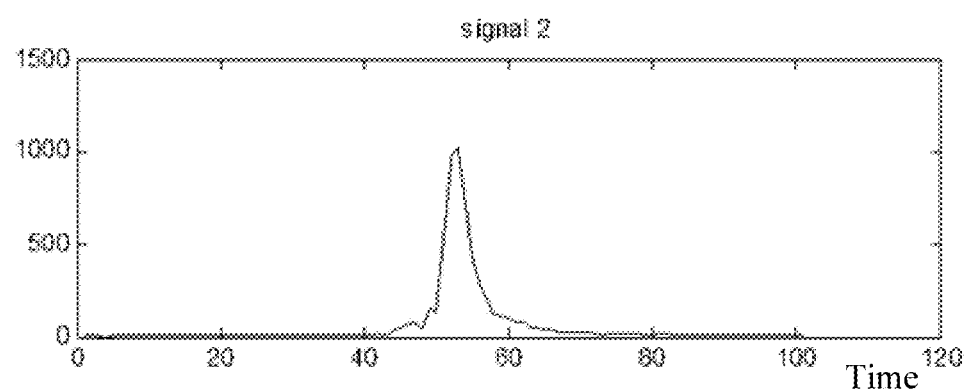

1) A phase encoding gradient magnetic field is closed. A spin echo signal and a stimulated-echo signal generated from each of the seven channels under the turbo spin echo sequence are acquired by performing a magnetic resonance pre-scanning. FIG. 5 illustrates a waveform diagram of the spin echo signal and the stimulated-echo signal corresponding to the channel 1 when the displacement of the stimulated-echo signal is 1. Where, signal1 is a waveform diagram of the spin echo signal, and signal2 is a waveform diagram of the stimulated-echo signal.

Figure 6:
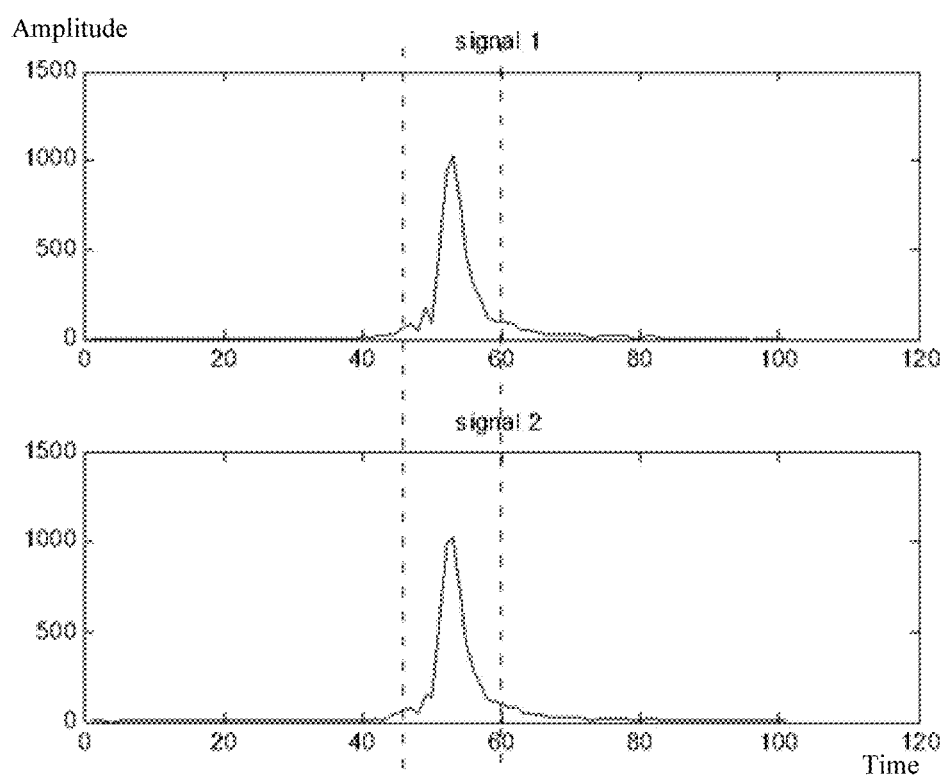
FIG. 6 illustrates a schematic diagram of a selected a data region on waveform diagrams of echo signals according to one or more examples of the present disclosure.

2) According to a preset threshold condition, a data region within the same time period is respectively selected from the first echo signal and the second echo signal for each of the 7 channels so that data in the data regions satisfies the threshold condition. As shown in FIG. 6, assuming that the threshold condition is 10% of the maximum amplitude of the stimulated-echo signal, the data regions represented in the dotted line range as shown in FIG. 6 may be selected according to the threshold condition. The amplitude of the data region represented within the dashed line range is 10-100% of the maximum amplitude. The data of the spin echo signal within the data region is denoted as $s1(i)$, and the data of the stimulated-echo signal in the data region is denoted as $s2(i)$, where i represents the position of the data.

3) A data window with a particular length may be selected in the data regions, and then weighted summation is performed on two signals in the data window to determine the phase difference between the spin echo signal and the stimulated-echo signal corresponding to the channel 1 when the displacement of the stimulated-echo signal is 1. And then the same calculation is performed on all the channels to obtain the phase difference between the spin echo signal and the stimulated-echo signal for each of the 7 channels when the displacement of the stimulated-echo signal is 2, 3, 4 and 5. In an example, assuming that the length of the data window is 5 and an index of a data midpoint is 0, the formula (1) for determining the phase difference may be as follows:

$$s=s1(-2)*s2(-2)+s1(-1)*s2(-1)\ldots+s2(2)**s2(2) \qquad (1)$$

Then, the signal curve of the stimulated-echo signal for each of the 7 channels is shifted under the displacements of 2 to 5, respectively, and the phase difference between the spin echo signal and the stimulated-echo signal for each of the channels is obtained.

Finally, the standard deviation of the phase difference between the spin echo signal and the stimulated-echo signal for all the channels under each of the displacements of 1 to 5 is determined as a standard deviation set. The result is shown in Table 1 below. It is to be noted that Dis1 indicates that the displacement for the stimulated-echo signal is 1, Dis2 indicates that the displacement for the stimulated-echo signal is 2, Dis3 indicates that the displacement for the stimulated-echo signal is 3, Dis4 indicates that the displacement for the stimulated-echo signal is 4, and Dis5 indicates that the displacement for the stimulated-echo signal is 5.

TABLE 1

|  | Channel 1 phase difference | Channel 2 phase difference | Channel 3 phase difference | Channel 4 phase difference | Channel 5 phase difference | Channel 6 phase difference | Channel 7 phase difference | Standard deviation |
|---|---|---|---|---|---|---|---|---|
| Dis1 | −0.4936 | −0.1870 | −0.6386 | −0.0390 | −0.3341 | 0.5709 | 0.4124 | 0.3845 |
| Dis2 | −0.0958 | 0.0118 | −0.1416 | 0.0578 | −0.0383 | 0.2658 | 0.2115 | 0.1409 |
| Dis3 | 0.3068 | 0.2198 | 0.3587 | 0.1671 | 0.2690 | −0.0293 | 0.0173 | 0.1350 |
| Dis4 | 0.7092 | 0.4244 | 0.8683 | 0.2726 | 0.5742 | −0.3270 | −0.1778 | 0.4131 |
| Dis5 | 1.0155 | 0.6323 | 1.2723 | 0.3862 | 0.7841 | −0.7266 | −0.4690 | 0.6933 |

4) A curve fitting is performed on a displacement corresponding to a minimum standard deviation among the standard deviation set, two displacements respectively before and after the displacement corresponding to the minimum standard deviation and their respective corresponding standard deviations to obtain a fitting curve, and a displacement corresponding to a minimum phase standard deviation on the fitting curve may be taken as the correction displacement. As shown in Table 1, the minimum standard deviation obtained from the standard deviation set is 0.1350, the corresponding displacement is the displacement 3, and two displacements respectively before and after the displacement 3 are the displacement 2 and the displacement 4. The curve fitting is then performed on the displacements 2 to 4 and their respective standard deviations (i.e., 0.1409, 0.1350, and 0.4131) corresponding to the displacements 2 to 4, and a displacement corresponding to a minimum phase standard deviation on the fitting curve may be taken as a correction displacement.

5) The correction displacement may be taken as a one-order phase correction value for the plurality of channels. The average value of the phase differences between the spin echo signal and the stimulated-echo signal for each of the plurality of channels under the correction displacement may be taken as a zero-order phase correction value for the plurality of channels.

Figure 7:
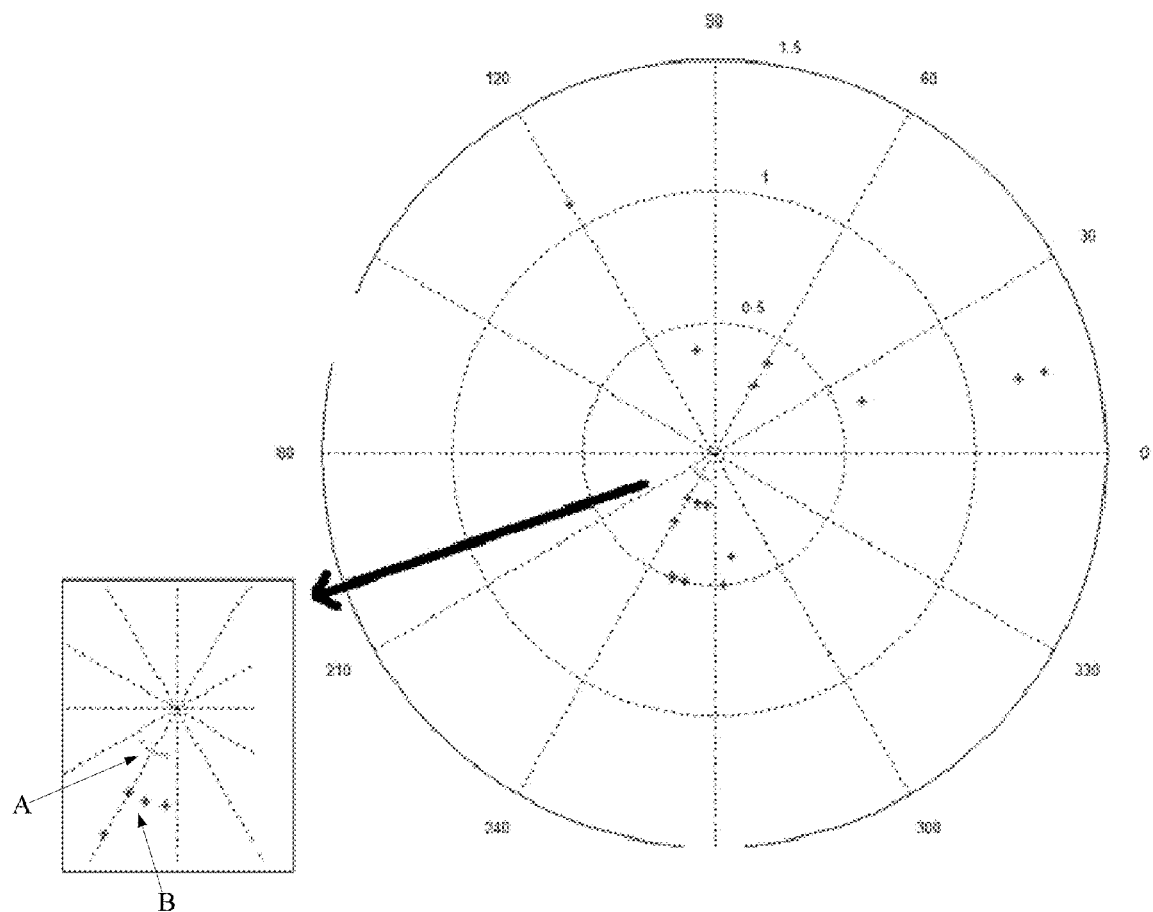
FIG. 7 illustrates a result of measured data according to one or more examples of the present disclosure.

FIG. 7 illustrates a result of measured data. It is noted that scanning parameters in FIG. 7 is set arbitrarily, without considering image quality. In FIG. 7, the length of a polar axis may correspond to the length of the one-order phase correction value, and the phase of the polar axis may correspond to the zero-order phase correction value. The solid point indicated by A in the polar coordinates diagram may indicate a corrected phase value obtained by the magnetic resonance imaging method in the present disclosure, and it may be found that the consistency degree between a plurality of corrected phase values is relatively high. The star point indicated by B in the polar coordinates diagram may indicate a corrected phase value obtained by the magnetic resonance imaging method in the prior art, and it may be found that a plurality of corrected phase values are more disperse and the obtained reconstructed image may be darker.

Figure 8:
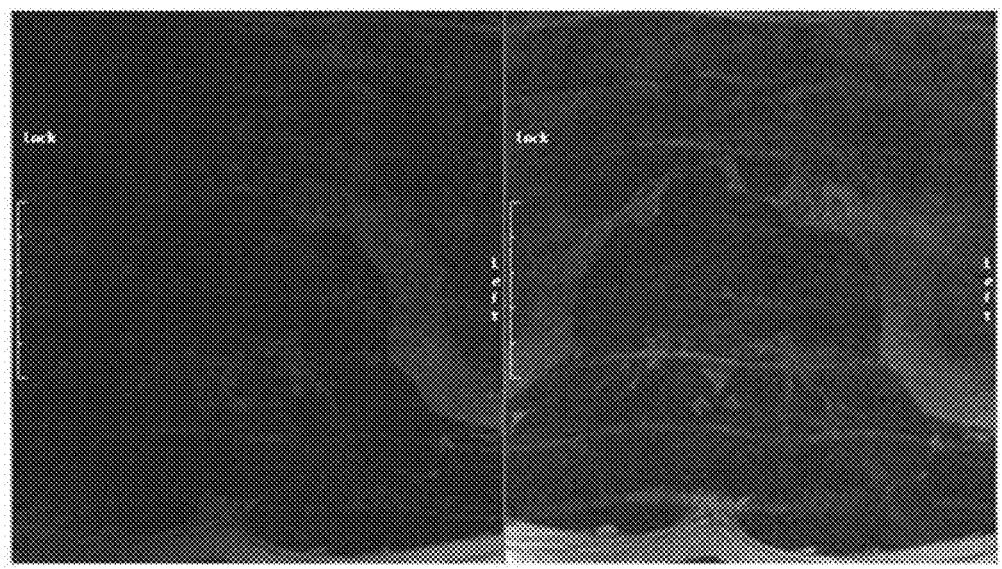
FIG. 8 illustrates a comparison diagram of magnetic resonance imaging results according to one or more examples of the present disclosure.

Two lumbar vertebrae diagrams shown in FIG. 8 are lumbar vertebrae comparison diagrams with the magnetic resonance imaging method in previous examples and the magnetic resonance imaging method in the present disclosure under a same scanning condition. The diagram shown on the left in FIG. 8 is a lumbar vertebrae diagram with the imaging method in previous examples, and the diagram shown on the right in FIG. 8 is a lumbar vertebrae diagram with the magnetic resonance imaging method in the present disclosure. By comparing the diagram shown on the left and the diagram shown on the right in FIG. 8, the reconstructed image with the magnetic resonance imaging method in the previous examples is darker. When the phase correction is performed with the magnetic resonance imaging method in the previous examples, the corrected phases may not be consistent, which may result in the image darkening. When the phase correction is performed with the magnetic resonance imaging method shown in the present disclosure, the corrected phases may be substantially consistent, and thereby image brightness is better.

Corresponding to examples of the magnetic resonance imaging method in the present disclosure described above, the present disclosure further provides one or more examples of a magnetic resonance imaging device.

Figure 9:
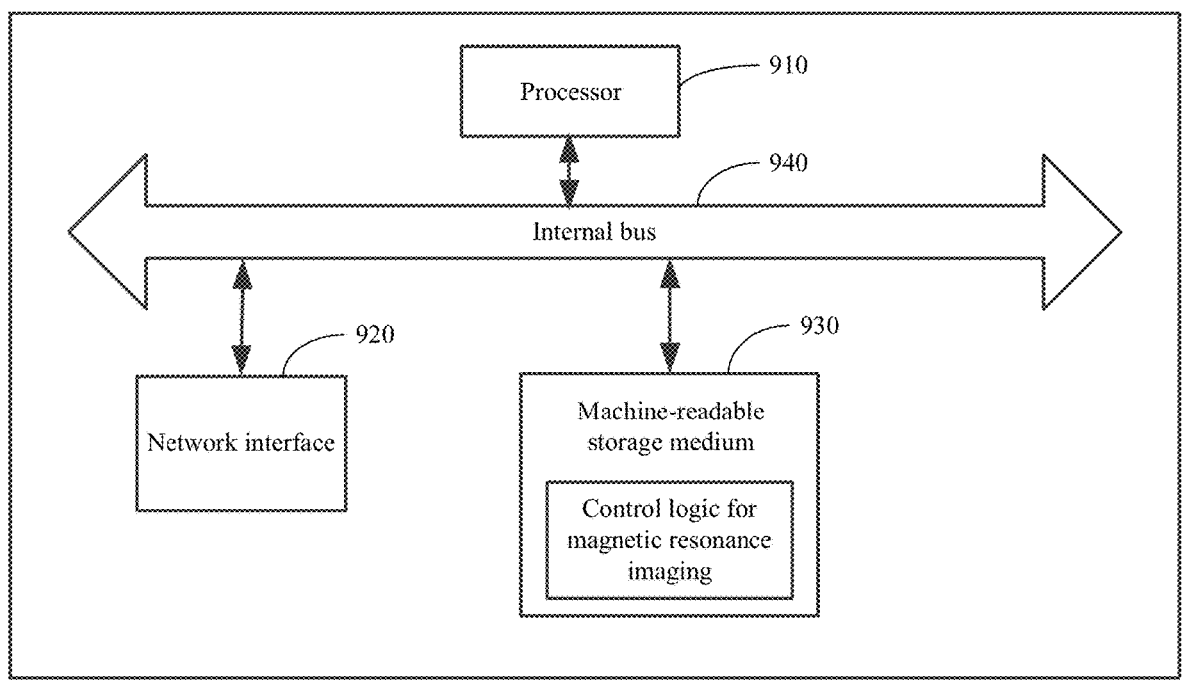
FIG. 9 illustrates a hardware structure diagram of a magnetic resonance imaging device according to one or more examples of the present disclosure.
Figure 10:
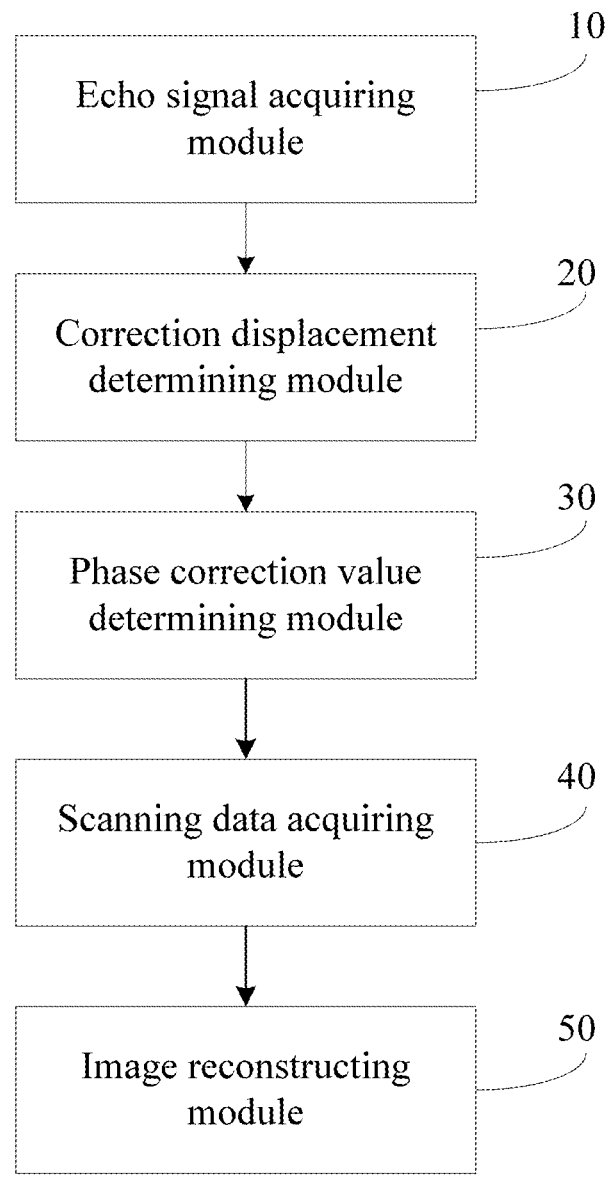
FIG. 10 illustrates a functional block diagram of control logic for magnetic resonance imaging according to one or more examples of the present disclosure.

FIG. 9 illustrates a hardware structure diagram of a magnetic resonance imaging device according to one or more examples of the present disclosure. The examples of the magnetic resonance imaging device may be implemented by software, or may be implemented by hardware or by a combination of hardware and software. From the hardware level, in addition to a processor 910, a network interface 920, a machine-readable storage medium 930, and an internal bus 940 shown in FIG. 9, the magnetic resonance imaging device may further include other hardware depending on actual functions, which will not be described herein. FIG. 9 will be described herein in combination with a method illustrated in FIG. 10.

In different examples, the machine-readable storage medium 930 may be a Read-Only Memory (ROM), a volatile memory, a non-volatile memory, a flash memory, a storage drive (e.g., a hard disk drive), a solid state hard disk, any type of storage disks (such as an optical disk, a DVD, etc.), or a similar storage medium, or a combination thereof.

Further, control logic for magnetic resonance imaging is stored on the machine-readable storage medium 930. As shown in FIG. 9, according to the functions, the control logic for magnetic resonance imaging may include the following of FIG. 10: an echo signal acquiring module 10, a correction displacement determining module 20, a phase correction value determining module 30, a scanning data acquiring module 40, and an image reconstructing module 50.

The echo signal acquiring module 10 is configured to acquire a first echo signal and a second echo signal generated from each of a plurality of channels of a magnetic resonance imaging device by performing a pre-scanning with the magnetic resonance imaging device according to an imaging sequence.

The correction displacement determining module 20 is configured to determine a correction displacement with which an imaging phase consistency for the plurality of channels is maximum by shifting a signal curve of the second echo signal for each of the plurality of channels for a plurality of times, where the imaging phase consistency indicates a phase consistency degree between the first echo signal and the shifted second echo signal for each of the plurality of channels.

The phase correction value determining module 30 is configured to determine a one-order phase correction value and a zero-order phase correction value for the plurality of channels under the imaging sequence according to the correction displacement.

The scanning data acquiring module 40 is configured to perform a formal scanning with the magnetic resonance imaging device according to the imaging sequence to obtain a set of scanning data.

The image reconstructing module 50 is configured to perform a phase correction on the set of scanning data according to the one-order phase correction value and the zero-order phase correction value to obtain a set of target scanning data for reconstructing an image.

In an example, the correction displacement determining module 20 may be further configured to provide a plurality of alternative displacements and shift the signal curve of the second echo signal for each of the plurality of channels according to each of the plurality of the alternative displacements. Where, during one shift, the displacements by which the signal curve of the second echo signal for each of the plurality of channels is shifted are the same.

In an example, the phase correction value determining module 30 is further configured to take the correction displacement as the one-order phase correction value for the plurality of channels under the imaging sequence; and take an average value of phase differences between the first echo signal and the second echo signal shifted according to the corrected displacement for each of the plurality of channels as the zero-order phase correction value for the plurality of channels under the imaging sequence.

Further, the correction displacement determining module 20 may be further configured to: determine a phase difference of each of the plurality of channels under each of the displacements by obtaining a phase difference between the first echo signal and the second echo signal shifted according to each of the displacements for each of the plurality of channels; determine a phase standard deviation for each of the displacements based on the phase difference of each of the plurality of channels under each of the displacements; and determine the correction displacement based on the phase standard deviation for each of the displacements.

In one or more examples of the present disclosure, when determining the correction displacement based on the phase standard deviation for each of the displacements, the correction displacement determining module 20 is further configured to: determine a displacement corresponding to a minimum value among the phase standard deviations as a first displacement; determine two displacements respectively before and after the first displacement, as a second displacement and a third displacement, respectively; obtain a fitting curve by performing a curve fitting with the first displacement, the second displacement, the third displacement and respective phase standard deviations corresponding to the first displacement, the second displacement, the third displacement; and take a displacement corresponding to a minimum phase standard deviation on the fitting curve as the correction displacement.

In one or more examples of the present disclosure, the correction displacement determining module 20 may be further configured to: respectively select a data region within a same time period from the first echo signal and the second echo signal shifted according to the displacement for the channel based on a preset threshold condition; and determine the phase difference between the first echo signal and the second echo signal shifted according to the displacement for the channel with data in the data regions.

In one or more examples of the present disclosure, the data in the data regions comprises two or more sets of data selected from a data window within any one or more of the data regions.

In one or more examples of the present disclosure, the echo signal acquiring module 10 may be further configured to: set a signal-to-noise ratio threshold; and select channels having a signal-to-noise ratio higher than the signal-to-noise ratio threshold from all channels of the magnetic resonance imaging device as the plurality of channels. In this way, the first echo signal and the second echo signal of a part of invalid channels may be filtered out to reduce the calculation amount and improve the efficiency during reconstructing the image.

The implementation processes of the functions and effects of each module in the above logic is described in detail in the implementation processes of the corresponding steps in the above method, and further description is omitted for brevity.

Taking the software implementation as an example, it is further described that how the magnetic resonance imaging device runs the control logic for magnetic resonance imaging. In this example, the control logic for magnetic resonance imaging of the present disclosure should be understood as machine-executable instructions stored in the machine-readable storage medium 930. When the processor 910 on the magnetic resonance imaging device of the present disclosure executes the control logic, the processor 910 may be caused to execute the above magnetic resonance imaging method by invoking the machine-executable instructions corresponding to the control logic stored on the machine-readable storage medium 930.

For simplicity and illustrative purposes, the present disclosure is described by referring mainly to examples thereof. In the above descriptions, numerous specific details are set forth to provide a thorough understanding of the present disclosure. It will be readily apparent however, that the present disclosure may be practiced without limitation to these specific details. In other instances, some methods and structures have not been described in detail so as not to unnecessarily obscure the present disclosure. As used herein, the terms "a" and "an" are intended to denote at least one of a particular element, the term "includes" means includes but not limited to, the term "including" means including but not limited to, and the term "based on" means based at least in part on.

The above description is merely preferred examples of the present disclosure and is not intended to limit the present disclosure in any form. Although the present disclosure is disclosed by the above examples, the examples are not intended to limit the present disclosure. Those skilled in the art, without departing from the scope of the technical scheme of the present disclosure, may make a plurality of changes and modifications of the technical scheme of the present disclosure by the method and technical content disclosed above.

Therefore, without departing from the scope of the technical scheme of the present disclosure, based on technical essences of the present disclosure, any simple alterations, equal changes and modifications should fall within the protection scope of the technical scheme of the present disclosure. Accordingly, other embodiments are within the scope of the following claims.

The invention claimed is:

1. A magnetic resonance imaging method, comprising:
   acquiring a first echo signal and a second echo signal generated from each of a plurality of channels of a magnetic resonance imaging device by performing a pre-scanning with the magnetic resonance imaging device according to an imaging sequence;
providing a plurality of alternative displacements;
shifting a signal curve of the second echo signal for each of the plurality of channels according to each of the plurality of alternative displacements;
determining a phase difference of each of the plurality of channels under each of the alternative displacements by obtaining a phase difference between the first echo signal and the second echo signal shifted according to each of the alternative displacements for each of the plurality of channels;
determining a phase standard deviation for each of the alternative displacements based on the phase difference of each of the plurality of channels under each of the alternative displacements;
determining a correction displacement based on the phase standard deviation for each of the alternative displacements;
determining a one-order phase correction value and a zero-order phase correction value for the plurality of channels under the imaging sequence according to the correction displacement;
performing a scanning with the magnetic resonance imaging device according to the imaging sequence to obtain a set of scanning data; and
performing a phase correction on the set of scanning data according to the one-order phase correction value and the zero-order phase correction value to obtain a set of target scanning data for reconstructing an image.

2. The method of claim 1, wherein determining the correction displacement based on the phase standard deviation for each of the alternative displacements comprises:
determining a displacement corresponding to a minimum value among the phase standard deviations as a first displacement;
determining two displacements respectively before and after the first displacement, as a second displacement and a third displacement, respectively;
obtaining a fitting curve by performing a curve fitting with the first displacement, the second displacement, the third displacement, and respective phase standard deviations corresponding to the first displacement, the second displacement, and the third displacement; and
taking a displacement corresponding to a minimum phase standard deviation on the fitting curve as the correction displacement.

3. The method of claim 2, wherein the curve fitting comprises:
a quadratic curve fitting.

4. The method of claim 1, wherein obtaining the phase difference between the first echo signal and the second echo signal shifted according to the alternative displacement for the channel comprises:
respectively selecting a data region within a same time period from the first echo signal and the second echo signal shifted according to the alternative displacement for the channel based on a preset threshold condition; and
determining the phase difference between the first echo signal and the second echo signal shifted according to the alternative displacement for the channel with data in the data regions.

5. The method of claim 4, wherein the data in the data regions comprises two or more sets of data selected from a data window within any one or more of the data regions.

6. The method of claim 4, wherein the preset threshold condition is 10% to 20% of a maximum amplitude of the first echo signal or the second echo signal.

7. The method of claim 4, wherein determining the phase difference between the first echo signal and the second echo signal shifted according to the alternative displacement for the channel comprises:
determining the phase difference between the first echo signal and the second echo signal shifted according to the alternative displacement for the channel with a weighted summation method.

8. The method of claim 1, further comprising:
setting a signal-to-noise ratio threshold; and
selecting channels having a signal-to-noise ratio higher than the signal-to-noise ratio threshold from all channels of the magnetic resonance imaging device as the plurality of channels.

9. The method according to claim 1, wherein determining the one-order phase correction value and the zero-order phase correction value for the plurality of channels under the imaging sequence comprises:
taking the correction displacement as the one-order phase correction value for the plurality of channels under the imaging sequence; and
taking an average value of phase differences between the first echo signal and the second echo signal shifted according to the corrected displacement for each of the plurality of channels as the zero-order phase correction value for the plurality of channels under the imaging sequence.

10. The method according to claim 1, wherein:
the imaging sequence is a turbo spin echo sequence,
the first echo signal is a spin echo signal, and
the second echo signal is a stimulated-echo signal.

11. A magnetic resonance imaging device, comprising:
a processor; and
a non-transitory machine-readable storage medium,
wherein by reading and executing machine-executable instructions corresponding to magnetic resonance imaging logic stored on the machine-readable storage medium, the processor is caused to:
acquire a first echo signal and a second echo signal generated from each of a plurality of channels of the magnetic resonance imaging device by performing a pre-scanning with the magnetic resonance imaging device according to an imaging sequence;
provide a plurality of alternative displacements;
shift a signal curve of the second echo signal for each of the plurality of channels according to each of the plurality of alternative displacements;
determine a phase difference of each of the plurality of channels under each of the alternative displacements by obtaining a phase difference between the first echo signal and the second echo signal shifted according to each of the alternative displacements for each of the plurality of channels;
determine a phase standard deviation for each of the alternative displacements based on the phase difference of each of the plurality of channels under each of the alternative displacements;
determine a correction displacement based on the phase standard deviation for each of the alternative displacements;
determine a one-order phase correction value and a zero-order phase correction value for the plurality of channels under the imaging sequence according to the correction displacement;

perform a scanning with the magnetic resonance imaging device according to the imaging sequence to obtain a set of scanning data; and perform a phase correction on the set of scanning data according to the one-order phase correction value and the zero-order phase correction value to obtain a set of target scanning data for reconstructing an image.

12. The device of claim 11, wherein, when determining the correction displacement based on the phase standard deviation for each of the alternative displacements, the processor is caused by the machine-executable instructions to:

determine a displacement corresponding to a minimum value among the phase standard deviations as a first displacement;

determine two displacements respectively before and after the first displacement, as a second displacement and a third displacement, respectively;

obtain a fitting curve by performing a curve fitting with the first displacement, the second displacement, the third displacement, and respective phase standard deviations corresponding to the first displacement, the second displacement, and the third displacement; and take a displacement corresponding to a minimum phase standard deviation on the fitting curve as the correction displacement.

13. The device of claim 11, wherein, when obtaining the phase difference between the first echo signal and the second echo signal shifted according to the alternative displacement for the channel, the processor is caused by the machine-executable instructions to:

respectively select a data region within a same time period from the first echo signal and the second echo signal shifted according to the alternative displacement for the channel based on a preset threshold condition; and determine the phase difference between the first echo signal and the second echo signal shifted according to the alternative displacement for the channel with data in the data regions.

14. The device of claim 13, wherein the data in the data regions comprises two or more sets of data selected from a data window within any one or more of the data regions.

15. The device of claim 11, wherein the processor is further caused by the machine-executable instructions to:

set a signal-to-noise ratio threshold; and select channels having a signal-to-noise ratio higher than the signal-to-noise ratio threshold from all channels of the magnetic resonance imaging device as the plurality of channels.

16. The device of claim 11, wherein, when determining the one-order phase correction value and the zero-order phase correction value for the plurality of channels under the imaging sequence, the processor is caused by the machine-executable instructions to:

take the correction displacement as the one-order phase correction value for the plurality of channels under the imaging sequence; and take an average value of phase differences between the first echo signal and the second echo signal shifted according to the corrected displacement for each of the plurality of channels as the zero-order phase correction value for the plurality of channels under the imaging sequence.

* * * * *